United States Patent
Wuerschmidt et al.

(10) Patent No.: US 12,280,193 B2
(45) Date of Patent: Apr. 22, 2025

(54) AUTOMATIC PRIMING OF AN EXTRACORPOREAL BLOOD TREATMENT DEVICE USING A PUSH-PULL METHOD

(71) Applicant: B. Braun Avitum AG, Melsungen (DE)

(72) Inventors: Tobias Wuerschmidt, Hann. Muenden (DE); Joana Sophie Schiller, Rheine (DE)

(73) Assignee: B. Braun Avitum AG, Melsungen (DE)

( * ) Notice: Subject to any disclaimer, the term of this patent is extended or adjusted under 35 U.S.C. 154(b) by 118 days.

(21) Appl. No.: 18/028,051

(22) PCT Filed: Sep. 17, 2021

(86) PCT No.: PCT/EP2021/075701
§ 371 (c)(1),
(2) Date: Mar. 23, 2023

(87) PCT Pub. No.: WO2022/063706
PCT Pub. Date: Mar. 31, 2022

(65) Prior Publication Data
US 2023/0256151 A1 Aug. 17, 2023

(30) Foreign Application Priority Data
Sep. 28, 2020 (DE) ...................... 10 2020 125 291.9

(51) Int. Cl.
*A61M 1/36* (2006.01)
*A61M 1/14* (2006.01)

(52) U.S. Cl.
CPC ............ *A61M 1/3621* (2013.01); *A61M 1/14* (2013.01); *A61M 2205/07* (2013.01)

(58) Field of Classification Search
CPC .. A61M 1/3621; A61M 1/14; A61M 2205/07; A61M 1/3629; A61M 1/3649; A61M 1/3652; A61M 1/365
(Continued)

(56) References Cited

U.S. PATENT DOCUMENTS

| 9,579,440 B2 | 2/2017 | Hogard et al. |
| 2009/0076433 A1* | 3/2009 | Folden ................ A61M 1/3649 604/4.01 |

(Continued)

FOREIGN PATENT DOCUMENTS

| CN | 110191729 A | 8/2019 |
| CN | 111278484 A | 6/2020 |

(Continued)

OTHER PUBLICATIONS

Search Report received in German Application No. 10 2020 125 291.9 dated Jun. 14, 2021, with translation, 11 pages.
(Continued)

*Primary Examiner* — Hayden Brewster
(74) *Attorney, Agent, or Firm* — Christopher A. Rothe; CM Law

(57) ABSTRACT

An extracorporeal blood treatment device and a method for automatic priming of an extracorporeal blood treatment device. The device includes an extracorporeal circuit, a dialyzer, a dialysis liquid circuit and a control unit. The control unit is designed to control the priming such that a liquid is delivered from the dialysis liquid circuit via a membrane of the dialyzer to the extracorporeal circuit, and to actuate valves and/or pumps in the dialysis liquid circuit such that pressure builds up in the dialyzer on the dialysis liquid side. The control unit actuates a flow machine in the (Continued)

extracorporeal circuit to perform a push cycle, in which the flow machine pushes air into the extracorporeal circuit, and a pull cycle, in which the flow machine draws air out from the extracorporeal circuit, to assist a transfer of the liquid through the membrane of the dialyzer during the priming process.

13 Claims, 3 Drawing Sheets

(58) Field of Classification Search
USPC .......................................................... 210/646
See application file for complete search history.

(56) References Cited

U.S. PATENT DOCUMENTS

| | | | |
|---|---|---|---|
| 2009/0084718 A1* | 4/2009 | Prisco | B01D 19/0042 |
| | | | 210/151 |
| 2010/0312162 A1* | 12/2010 | Masaoka | A61M 1/3649 |
| | | | 604/6.11 |
| 2012/0265117 A1* | 10/2012 | Fava | A61M 1/30 |
| | | | 604/6.09 |
| 2013/0199998 A1* | 8/2013 | Kelly | A61M 1/3482 |
| | | | 210/85 |
| 2018/0028739 A1* | 2/2018 | Mishkin | A61M 1/3417 |
| 2019/0321533 A1 | 10/2019 | Hacker et al. | |
| 2020/0061273 A1 | 2/2020 | Hogard et al. | |
| 2020/0338255 A1 | 10/2020 | Hobro et al. | |
| 2021/0093773 A1* | 4/2021 | Bocz | A61M 1/3626 |
| 2022/0105252 A1* | 4/2022 | Noack | G01F 1/36 |

FOREIGN PATENT DOCUMENTS

| | | |
|---|---|---|
| DE | 10011208 C1 | 9/2001 |
| DE | 102019101542 A1 | 7/2020 |
| EP | 1457218 A1 | 9/2004 |
| EP | 2361643 B1 | 6/2016 |
| EP | 3127564 B1 | 12/2018 |

OTHER PUBLICATIONS

Search Report received in International Application No. PCT/EP2021/075701 dated Dec. 14, 2021, with translation, 5 pages.
Written Opinion received in International Application No. PCT/EP2021/075701 dated Dec. 14, 2021, with translation, 13 pages.
Office Action received in Chinese Application No. 202180065949.8 dated Dec. 14, 2023, with translation, 10 pages.

* cited by examiner

AUTOMATIC PRIMING OF AN EXTRACORPOREAL BLOOD TREATMENT DEVICE USING A PUSH-PULL METHOD

CROSS-REFERENCE TO RELATED APPLICATIONS

This application is the United States national phase entry of International Application No. PCT/EP2021/075701, filed on Sep. 17, 2021, which published as International Publication No. WO 2022/063706 A1 on Mar. 31, 2022, and claims priority to German Application No. 10 2020 125 291.9, filed on Sep. 28, 2020. The contents of International Application No. PCT/EP2021/075701 and German Application No. 10 2020 125 291.9 are incorporated by reference herein in their entireties.

FIELD

The present disclosure relates to an extracorporeal blood treatment device, in particular a dialysis machine, which is prepared or configured for automatic priming thereof. Furthermore, the present disclosure relates to a method for automatically priming an extracorporeal blood treatment device.

BACKGROUND

Extracorporeal (blood) circuits for carrying blood outside a patient's body during a blood purification procedure are known from practice. Such extracorporeal circuits are filled with a priming solution or priming liquid, respectively, prior to the start of a treatment. This filling of the extracorporeal circuit and a dialyzer with priming solution (e.g. NaCl) or priming liquid (priming), respectively, serves to prepare the extracorporeal circuit and the dialyzer for the subsequent treatment. In particular, priming serves to displace air still present in the extracorporeal circuit and in the dialyzer prior to treatment with a physiologically compatible liquid or solution in order to prevent this air from entering the patient's vascular system during and in particular at the beginning of the blood treatment.

In addition to priming or the priming process, the extracorporeal circuit and the dialyzer are usually subjected to flushing or a flushing process in order to prepare the extracorporeal circuit and the dialyzer for the subsequent treatment. Flushing or the flushing process is usually performed simultaneously or (immediately) after priming or the priming process. Flushing or the flushing process serves in particular to flush residual substances/pyrogens out of the extracorporeal circuit and out of the dialyzer, in particular out of a membrane thereof. Such residual substances/pyrogens may originate from a production, packaging or set-up process and represent a potential hazard to the patient.

When the dialyzer and a hose system forming the extracorporeal (blood) circuit have been prepared, i.e. when priming and flushing of the latter have been performed, the patient can basically be connected, and the priming or rinsing fluid is drained from the completely filled system and is replaced on one side by the patient's blood.

The present disclosure relates in particular to priming, i.e., preparation of the extracorporeal blood treatment device. In other words, connection/treatment of a patient is preferably not a subject matter of the present disclosure, so that, according to the disclosure, preferably no contact of the extracorporeal blood treatment device with a patient is provided.

Priming via an external saline bag is known from the prior art. A saline bag is connected to a hose of the extracorporeal circuit (to one side of the bloodline system) and the priming liquid is filled into the hose system and the dialyzer. In order to ensure that the dialyzer is properly filled with liquid, it has to be rotated in between in order to remove any remaining air bubbles from the system. The used liquid is collected in an empty bag.

Furthermore, so-called online priming is known from the prior art. In online priming, dialysis liquid is provided by the blood treatment device and added to the blood tubing system and the dialyzer via a substitute connection using an arterial blood pump. With this priming method, the dialyzer also has to be rotated in order to remove any remaining air bubbles from the system.

These two priming methods have the disadvantage that manual steps are always required by the user, for example when rotating the dialyzer. Due to high pressure on costs and sometimes strict guidelines (e.g. of the Center for Disease Control and Preventions in the United States), automatic preparation, in particular automatic priming, of the extracorporeal blood treatment device is desirable. Preferably, no saline bags and no disposable items or, respectively, as few disposable items as possible, which have to be removed and disposed of prior to therapy, should be used.

It is also known from the prior art that dialysis liquid/dialysate (instead of a saline solution) is used for priming. In this case, the dialysis liquid is transported via a membrane of the dialyzer into the blood hose system. If the arterial and venous blood hose lines are short-circuited here, dialysis liquid can be pumped into the dialyzer and the blood hose system from the dialysis liquid side via a suitable pump actuation and via suitable valve actuations, and these can thus be filled. In this context, reference is made, for example, to EP 3 127 564 B1 or EP 1 457 218 A1.

Further automatic priming methods are known, for example, from U.S. Pat. No. 9,579,440 B2 or EP 2 361 643 B1.

In particular, the prior art has the disadvantage that no suitable automatic priming methods exist that can be used equally for high-flux dialyzers (large pores in the dialyzer membrane) and for low-flux dialyzers (small pores in the dialyzer membrane). In particular, in the prior art, low-flux dialyzers have always proven difficult to deliver dialysis liquid via the dialyzer membrane into the blood hose system/extracorporeal circuit.

SUMMARY

Against this background, the object of the present disclosure is to provide improved automatic priming of a blood treatment device which can be used equally for high-flux dialyzers and for low-flux dialyzers. In particular, an automatic priming method is to be provided which enables dialysis liquid to be conveyed in a suitable manner via the dialyzer membrane into the blood hose system/extracorporeal circuit even in the case of low-flux dialyzers. The aim is to reduce the number of required disposables/disposable items or, preferably, to require only a few or no additional disposables/disposable items and no substitution connection.

The disclosure relates first to an extracorporeal blood treatment device prepared for automatic priming thereof, comprising: an extracorporeal circuit, a dialyzer, a dialysis liquid circuit and a control unit, wherein the extracorporeal circuit and the dialysis liquid circuit are separated from each other via a membrane provided in the dialyzer, wherein the control unit is configured to control the priming in such a way that a liquid, in particular priming/dialysis liquid, is supplied from the dialysis liquid circuit via the membrane of the dialyzer to the extracorporeal circuit, and to control valves and/or pumps provided in the dialysis liquid circuit in such a way that a pressure build-up takes place in the dialyzer on the dialysis liquid side, wherein the control unit controls a flow machine, in particular a compressor or pump, provided in the extracorporeal circuit, in particular cyclically alternating, to perform a push/or press cycle, in which the flow machine pushes air into the extracorporeal circuit and a pull/or suck cycle, in which the flow machine pulls air out of the extracorporeal circuit, in order to support a transfer of the liquid via the membrane of the dialyzer during priming.

According to the disclosure, automatic priming (by a suitable control) is thus basically provided, in which a pressure is built up in the dialyzer on the dialysis liquid side/in the dialysis liquid circuit. This pressure build-up can basically take place in any way by controlling pumps (e.g. flux-pump inlet and flux-pump outlet) or valves (e.g. dialyzer inlet valve and dialyzer outlet valve) provided in the dialysis liquid circuit. The pressure build-up is essentially achieved by pressing more liquid, in particular dialysis liquid, into the dialyzer than can flow out of the dialyzer. In principle, it is also conceivable that the liquid can no longer flow out of the dialyzer at all, for example by closing the valve at the dialyzer outlet (dialyzer outlet valve). The pressure build-up in the dialyzer on the dialysis liquid side results in a large negative transmembrane pressure (TMP).

In particular, the present disclosure enables liquid transfer from the side of the dialysis liquid circuit via the membrane of the dialyzer to the extracorporeal circuit to be supported, and at the same time the maximum permissible transmembrane pressure is not exceeded according to amount (i.e. the (negative) predetermined threshold value is not undershot). The maximum transmembrane pressure depends on the dialyzer type/the dialyzer used, and is always specified in the dialyzer data sheets.

In particular, according to the disclosure, a push-pull control or push-pull method is provided, which is realized by suitable controlling of a flow machine provided in the extracorporeal circuit (the blood side). This push-pull method is preferably divided into two cycles, namely the press/or push cycle and the suck/or pull cycle.

In the suck/or pull cycle, air is basically sucked out of the extracorporeal circuit, so that a transfer of dialysis liquid through the membrane of the dialyzer is supported and thus facilitated. However, the transmembrane pressure increases in a disadvantageous manner according to amount, so that on the one hand there is a risk that the maximum permissible transmembrane pressure is exceeded (according to amount), and on the other hand there is a risk that an air trap provided in the extracorporeal circuit collapses due to the negative pressure (underpressure) generated.

Therefore, according to the disclosure, it is necessary that the suck/or pull cycle is not carried out for too long and that the suck/or pull cycle is followed by a press/or push cycle. During the press/or push cycle, air is preferably pushed (by the flow machine provided in the extracorporeal circuit) into the hose system/the extracorporeal circuit, so that the negative pressure prevailing in the extracorporeal circuit is neutralized. Thus, only a neutralization of the negative pressure takes place in the press/or push cycle, i.e., no overpressure is generated or built up.

In other words, the press/or push cycle influences the transmembrane pressure positively, i.e. the transmembrane pressure increases or decreases according to amount (negative pressure), and the suck/or pull cycle influences the transmembrane pressure negatively, i.e. the transmembrane pressure decreases or increases according to amount (negative pressure). By driving the flow machine on the side of the extracorporeal circuit according to the disclosure, it is achieved that the liquid transfer via the membrane of the dialyzer is supported in a suitable manner, and at the same time the maximum permissible transmembrane pressure is not exceeded according to amount, and an air trap provided in the extracorporeal circuit is not collapsed.

Overall, the present disclosure enables automatic priming with low-flux dialyzers. In particular, the push-pull method according to the disclosure or the push-pull control according to the disclosure achieves a suitable liquid transfer via the membrane of the dialyzer even with low-flux dialyzers (small pores). However, the present disclosure is not limited to low-flux dialyzers. In particular, it is valid that the method according to the disclosure or the control according to the disclosure can also be applied to high-flux dialyzers. Generally, according to the present disclosure, a low-flux dialyzer is understood to be a dialyzer having an ultrafiltration coefficient KUF of less than or equal to 15 ml/(h*mmHg) (hourly ultrafiltration in ml achieved per mmHg transmembrane pressure (TMP)), and a high-flux dialyzer is understood to be a dialyzer having an ultrafiltration coefficient KUF of greater than 15 ml/(h*mmHg).

It is advantageous if a flux-pump inlet is provided in the dialysis liquid circuit upstream of the dialyzer and a flux-pump outlet is provided downstream of the dialyzer, and the control unit is configured to drive the flux-pump inlet and the flux-pump outlet to build up pressure in the dialyzer on the dialysis liquid side in such a way that a flow rate of the flux-pump inlet is greater than a flow rate of the flux-pump outlet. This ensures that more liquid is pressed into the dialyzer by the flux-pump inlet than is withdrawn by the flux-pump outlet, so that a suitable pressure build-up can take place in the dialyzer.

Preferably, the flux-pump inlet and the flux-pump outlet are operated with a flow rate difference of 300 ml/min to 500 ml/min, particularly preferably of about/approximately 400 ml/min. This means that the flow rate of the flux-pump inlet is preferably 300 ml/min to 500 ml/min, particularly preferably about 400 ml/min greater than the flow rate of the flux-pump outlet.

Preferably, the flow machine provided in the extracorporeal circuit is a compressor or a level regulation pump, respectively, which is arranged downstream of an expansion chamber or air trap (e.g., a venous air trap or an arterial air trap) provided in the extracorporeal circuit, or which is connected to the air trap, and which presses the air into the air trap or sucks it out of the air trap. Such a compressor or gauge/level regulation pump is often installed or integrated in extracorporeal blood treatment devices or dialysis machines as standard and is usually used to adjust the level of the air trap. If this compressor or level regulation pump is used for the push-pull control of the present disclosure, no hardware changes have to be made to the dialysis machine according to the prior art, but only software changes.

Advantageously, the control unit is configured to cyclically change/alternate/repeat the push/or press cycle and the pull/or suck cycle. In other words, the push/or press cycle and the pull/or suck cycle are executed multiple times and repeatedly. For example, the push cycle may be executed first, then the pull cycle, then the push cycle again, then the pull cycle, and so on. However, it is also conceivable that the pull cycle is executed first, then the push cycle, then the pull cycle again, and so on. In other words, the push-pull method according to the disclosure or the push-pull control according to the disclosure is characterized in particular by the cyclic repetition/changing/ alternation of the push cycle and the pull cycle.

Preferably, the control unit is configured to stop the cyclic alternation of the push/or press cycle and the pull/or suck cycle when a safety air detector provided in the venous portion of the extracorporeal circuit detects the liquid, in particular dialysis liquid. In other words, according to the disclosure, the push and pull cycles are alternated and repeated until the stop criterion mentioned herein is met.

Advantageously, the dialyzer is a low-flux dialyzer with an ultrafiltration coefficient of less than or equal to 15 ml/(h*mmHg). In particular, according to the disclosure, it has been found that with the push-pull control described, it is possible to automatically prime not only a high-flux dialyzer, but also via a low-flux dialyzer in a suitable manner.

Preferably, the control unit is configured to switch between the push/or press cycle and the pull/or suck cycle in a sensor-controlled and/or time-controlled manner. According to the present disclosure, the change between push cycle and pull cycle and vice versa can thus be made when a predetermined period of time has elapsed. However, it is also conceivable that pressures in the extracorporeal circuit and/or in the dialysis liquid circuit are measured via (pressure) sensors provided in the extracorporeal circuit and/or in the dialysis liquid circuit, and the change between push cycle and pull cycle is made based on the information received from the sensor(s). For example, a transmembrane pressure can be calculated from the measured pressures, and a sensor-controlled change between push cycle and pull cycle can be made based on the calculated transmembrane pressure. In principle, however, it is also conceivable according to the disclosure that both information from sensors and time aspects are taken into account when changing between push cycle and pull cycle, so that the change can in principle also be made in a sensor-controlled and time-controlled manner.

According to an advantageous aspect of the present disclosure, the control unit is configured to first perform the push/or press cycle and to perform the pull/or suck cycle after performing the push/or press cycle for the first time. In particular, according to the disclosure, it has been found that when the press cycle is performed at the beginning of the method/control, the liquid, in particular dialysis liquid, in the extracorporeal circuit does not pass uncontrolled to a pressure sensor/to the flow machine/to a possibly provided hydrophobic filter (before the pressure sensor or the flow machine).

An advantageous configuration example of the present disclosure is characterized in that the control unit is configured to switch from the push/or press cycle to the pull/or suck cycle when a transmembrane pressure exceeds a first predetermined threshold value, and to switch from the pull/or suck cycle to the push/or press cycle when the transmembrane pressure falls below a second predetermined threshold value.

In principle, the transmembrane pressure increases or decreases according to amount (negative value) in the push cycle. When the transmembrane pressure is or becomes greater than the first predetermined threshold value, the change to the pull cycle takes place. According to the disclosure, it has been found that the first predetermined threshold value should preferably be set at approximately/ rounded/about −400 mmHg. In the pull cycle, the transmembrane pressure decreases or increases according to amount (negative value). When the transmembrane pressure is or becomes smaller than the second predetermined threshold value, the change to the push cycle takes place. According to the disclosure, it has been found that the second predetermined threshold value should preferably be set at approximately/rounded/about −420 mmHg.

Thus, the first predetermined threshold value is preferably greater than the second predetermined threshold value.

Preferably, the control unit is configured to change between the push/or press cycle and the pull/or suck cycle depending on the dialyzer used. In other words, according to the disclosure, it may be provided that the push-pull method or the push-pull control is performed depending on the dialyzer used (high-flux dialyzer or low-flux dialyzer), i.e. that the control for a high-flux dialyzer differs from the control for a low-flux dialyzer.

Furthermore, the present disclosure relates to a method for automatically priming an extracorporeal blood treatment device comprising an extracorporeal circuit, a dialyzer and a dialysis liquid circuit, comprising the steps of: priming the extracorporeal circuit and the dialyzer by supplying a liquid from the dialysis liquid circuit to the extracorporeal circuit via a membrane of the dialyzer; building up a pressure in the dialyzer on the dialysis liquid side by suitably controlling or actuating valves and/or pumps provided in the dialysis liquid circuit; and performing a push/or press cycle, in which a flow machine, in particular a compressor or pump, provided in the extracorporeal circuit pushes air into the extracorporeal circuit, and a pull/or suck cycle, in which the flow machine pulls air out of the extracorporeal circuit to support transfer of the liquid via the membrane of the dialyzer during priming.

Preferably, the method further comprises the step of: operating a flux-pump inlet upstream of the dialyzer at a flow rate that is greater than a flow rate of a flux-pump outlet downstream of the dialyzer.

Advantageously, the method further comprises the step of: pushing air into and pulling air from an expansion chamber provided in the extracorporeal circuit by a compressor or a gauge/level regulation pump, respectively.

Furthermore, it is advantageous if the method comprises the following step: cyclically alternating and repeating the push/or press cycle and the pull/or suck cycle.

Preferably, the method further comprises the following step: stopping the cyclic alternation of the push/or press cycle and the pull/or suck cycle when a safety air detector provided in a venous portion of the extracorporeal circuit detects the liquid, in particular dialysis liquid.

The method preferably further comprises the step of: time-controlled and/or sensor-controlled changing between the push/or press cycle and the pull/or suck cycle.

Preferably, in accordance with the method according to the disclosure, the push/or press cycle is performed first, and after the push/or press cycle has been performed for the first time, the pull/or suck cycle is performed.

Advantageously, the method further comprises the step of: changing from the push/or press cycle to the pull/or suck cycle when a transmembrane pressure exceeds a first predetermined threshold value, and changing from the pull/or suck cycle to the push/or press cycle when the transmembrane pressure falls below a second predetermined threshold value.

BRIEF DESCRIPTION OF THE DRAWINGS

The disclosure is further explained below with reference to figures. The following is shown.

DETAILED DESCRIPTION

The figures are merely schematic in nature and are intended solely for the purpose of understanding the present disclosure. Identical elements are designated with the same reference signs. The features of the individual configuration examples can be interchanged.

Figure 1:
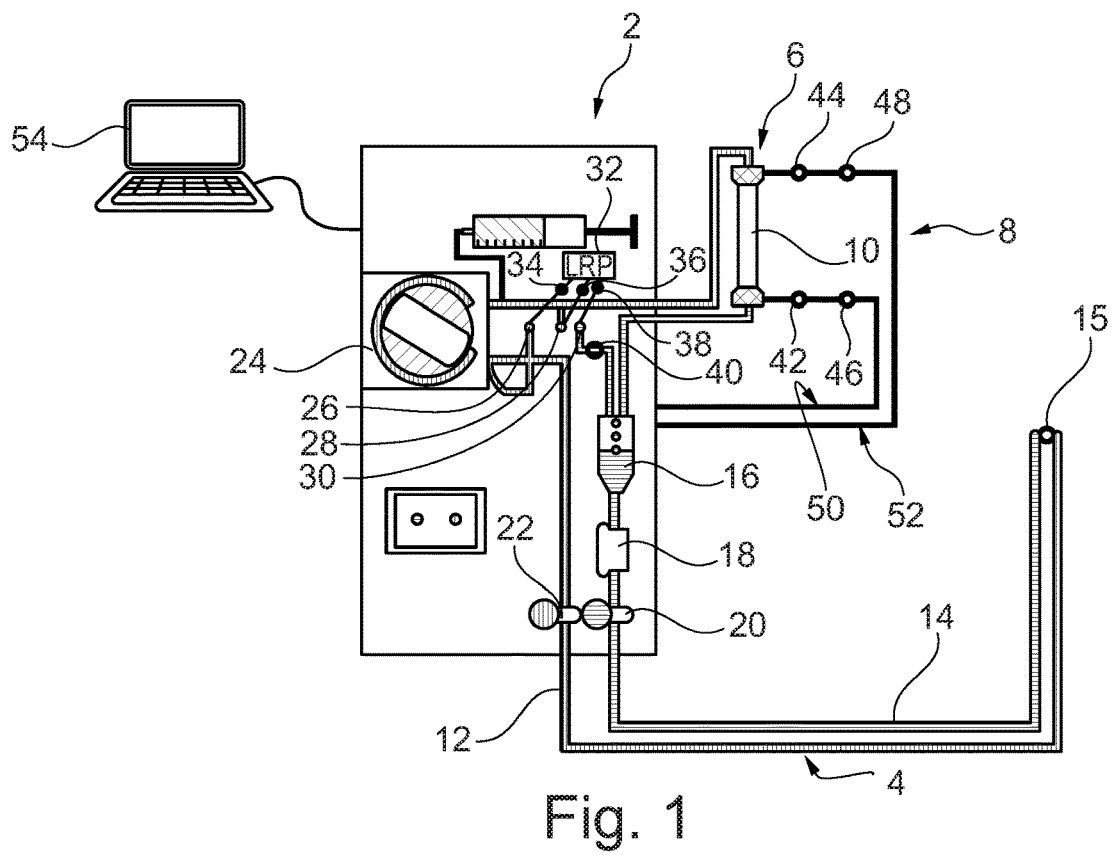
FIG. 1 shows an extracorporeal blood treatment device according to a first preferred configuration example of the present disclosure.

FIG. 1 shows an extracorporeal blood treatment device (dialysis machine) 2 according to a first preferred configuration example of the present disclosure.

The extracorporeal blood treatment device 2 basically includes an extracorporeal circuit (A/V hose system) 4, a dialyzer 6, and a dialysis liquid circuit 8. Wherein the extracorporeal circuit 4 and the dialysis liquid circuit 8 are separated from each other by a membrane 10 provided in the dialyzer 6.

The extracorporeal circuit 4 includes an arterial portion 12 located upstream of the dialyzer 6 and a venous portion 14 located downstream of the dialyzer 6.

As shown in FIG. 1, the arterial portion 12 and the venous portion 14 are connected/short-circuited via an adapter or connector 15. In other words, one end of the arterial portion 12 as well as one end of the venous portion 14 are inserted into the adapter 15 to fluidically connect the arterial portion 12 and the venous portion 14. Preferably, two Luer connections, which are preferably provided at the ends of the arterial portion 12 and of the venous portion 14, may be inserted into the adapter 15.

In the venous portion 14 of the extracorporeal circuit 4, downstream of the dialyzer 6 (that is, starting from the dialyzer 6 in a direction toward the end of the venous portion 14), a venous expansion chamber or air trap 16, a venous safety air detector 18, and a venous hose clamp 20 are provided.

In the arterial portion 12, starting from the adapter 15 in a direction towards the dialyzer 6, an arterial hose clamp 22 and an (arterial) blood pump 24 are provided. As can be seen in FIG. 1, the extracorporeal circuit 4 (in particular a blood-pump adapter thereof) is already inserted into the blood pump 24, which is preferably formed as a roller pump or peristaltic pump and is configured to convey a fluid/liquid by squeezing a hose.

In the arterial portion 12, an arterial pressure upstream or respectively before the blood pump 24 can be measured by an arterial pressure sensor 26. Furthermore, a dialyzer inlet pressure can be measured downstream or respectively after the blood pump 24 and upstream or respectively before the dialyzer 6 (between dialyzer 6 and blood pump 24) via a dialyzer-inlet pressure sensor 28. In the venous portion 14, venous pressure at/downstream of the venous expansion chamber or air trap 16 can be measured via a venous pressure sensor 30. The pressure sensors 26, 28, 30 provided in the extracorporeal circuit 4 can measure/take/monitor the pressure at the respective locations in the extracorporeal circuit 4 where they are arranged/provided.

As can be furthermore seen from FIG. 1, a compressor or gauge or level regulation pump (LRP) 32 (as an example of a flow machine according to the present disclosure) is located downstream of the arterial pressure sensor 26, the dialyzer-inlet pressure sensor 28 and the venous pressure sensor 30 and has associated valves 34, 36, 38, namely a first valve 34 between the arterial pressure sensor 26 and the gauge or level regulation pump 32, a second valve 36 between the dialyzer-inlet pressure sensor 28 and the gauge or level regulation pump 32, and a third valve 38 between the venous pressure sensor 30 and the gauge or level regulation pump 32.

A hydrophobic filter 40 is provided between the venous expansion chamber 16 and the venous pressure sensor 30 and allows liquid to be kept away from the venous pressure sensor 30 and the gauge or level regulation pump 32.

The dialysis liquid circuit 8 includes a dialyzer inlet valve 42, a dialyzer outlet valve 44, a flux-pump inlet 46, and a flux-pump outlet 48. The dialyzer inlet valve 42 and the flux-pump inlet 46 are provided/arranged at a dialysis liquid inflow 50 upstream of the dialyzer 6. The dialyzer outlet valve 44 and the flux-pump outlet 48 are provided/arranged at a dialysis liquid outflow 52 downstream of the dialyzer 6. The flux-pump inlet 46 and the flux-pump outlet 48 are preferably gear pumps.

The extracorporeal blood treatment device 2 further comprises a control unit 54, which is preferably formed as a processor, in particular as a central processing unit (CPU). The control unit 54 receives information from sensors which are provided in the extracorporeal blood treatment device 2. The sensors shown in FIG. 1 are merely exemplary, i.e. the arterial pressure sensor 26, the dialyzer-inlet pressure sensor 28, the venous pressure sensor 30, the venous safety air detector 18, etc. On the other hand, the control unit 54 controls or operates actuators which are provided in the extracorporeal blood treatment device 2. The valves or pumps shown in FIG. 1, i.e. in particular the dialyzer inlet valve 42, the dialyzer outlet valve 44, the flux-pump inlet 46, the flux-pump outlet 48, the (arterial) blood pump 24, the valves 34, 36, 38, etc. are merely examples.

Figure 2:
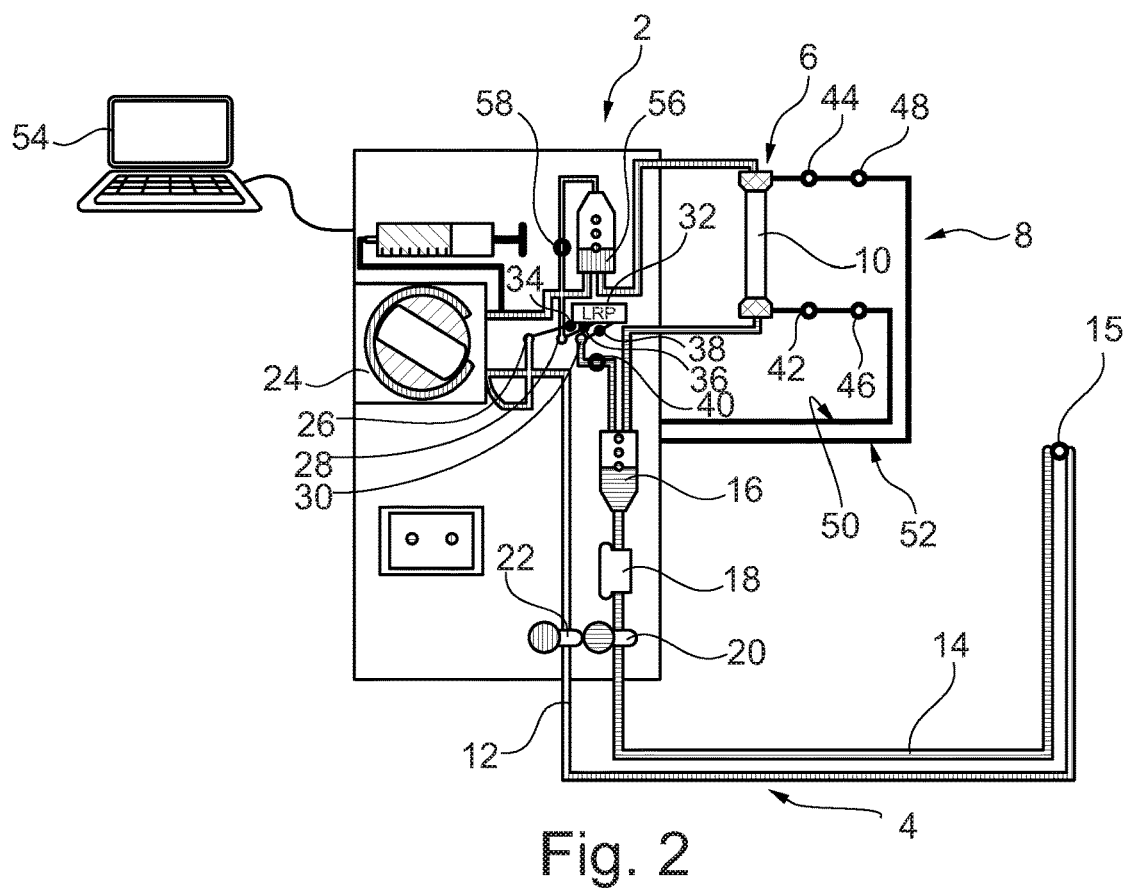
FIG. 2 shows an extracorporeal blood treatment device according to a second preferred configuration example of the present disclosure.

FIG. 2 shows an extracorporeal blood treatment device (dialysis machine) 2 according to a second preferred configuration example of the present disclosure. As can be seen from FIG. 2, the second preferred configuration example is very similar to the first preferred configuration example, so that the preceding explanations or descriptions apply mutatis mutandis to the structure shown in FIG. 2 and are therefore not repeated. Against this background, only the differences of the second embodiment compared to the first embodiment will be explained in the following explanations.

As shown in FIG. 2, in addition to the venous expansion chamber or air trap 16, the extracorporeal circuit 4 also has an arterial expansion chamber or air trap 56. The arterial expansion chamber 56 is connected or coupled to the dialyzer-inlet pressure sensor 28.

According to this configuration example, the compressor or gauge/level regulation pump 32 can push air into or pull air out of both the arterial expansion chamber 56 and the venous expansion chamber 16, respectively, i.e., the compressor or gauge/level regulation pump 32 can perform its function according to the disclosure both at the arterial expansion chamber 56 and at the venous expansion chamber 16. However, as shown in FIG. 2, the gauge/level regulation pump 32 cannot work in opposite ways at the two expansion chambers 16, 56, i.e. it cannot perform opposite functions. That is, the gauge/level regulation pump 32 cannot push air into the extracorporeal circuit 4 at one air trap 16 or 56 and remove air from the extracorporeal circuit 4 at the other air trap 56 or 16. However, separate controlling of the air traps 16, 56 is possible by either disconnecting the venous air trap 16 from the gauge/level regulation pump 32 through the third valve 38 (to control the arterial air trap 56) or disconnecting the arterial air trap 56 from the gauge/level regulation pump 32 through the second valve 36 (to control the venous air trap 16).

As further shown in FIG. 2, a hydrophobic filter 58 is also provided between the arterial air trap 56 and the dialyzer-inlet pressure sensor 28, which allows liquid to be kept away from the dialyzer-inlet pressure sensor 28 and the gauge or level regulation pump 32.

Figure 3:
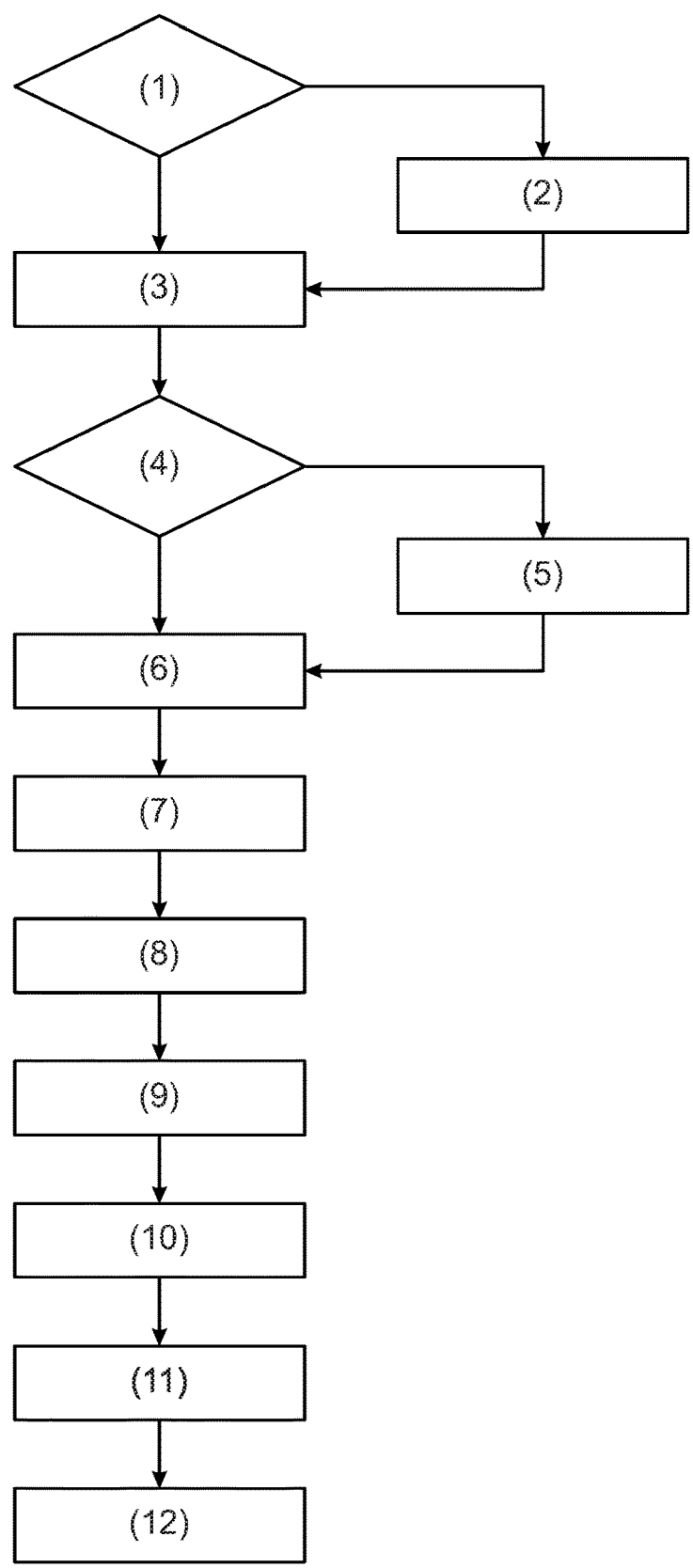
FIG. 3 shows a flowchart of an automatic priming method according to the present disclosure.

FIG. 3 shows a flow diagram of a method sequence of the automatic priming according to the present disclosure. The method sequences of the two configuration examples shown in FIG. 1 and FIG. 2 are basically very similar, so that in the following explanations only differences between the respective method and/or program sequences will be discussed.

At the start of the method, it is checked at (1) 'membrane movement?' whether a membrane is moving in a balance chamber (not shown) in the extracorporeal blood treatment device 2. If this is the case (YES), the membrane in the balance chamber is set at (2) 'set membrane'. This sets the balance chamber to flow, allowing the flux-pump inlet 46 and flux-pump outlet 48 to generate different flows or flow rates, respectively. If no membrane movement is detected (NO) or if the membrane has been set, the method proceeds from (1) or (2) to (3) 'fill dialyzer on dialysis fluid side'.

In (3), the dialyzer 6 is filled with (dialysis) liquid on the dialysis liquid side. For this purpose, the valves and pumps provided in the dialysis liquid circuit 8 are controlled in a suitable manner. Preferably, the flux-pump inlet 46 and the flux-pump outlet 48 are operated with a (slight) flow-rate difference. For example, the flow rate of the flux-pump inlet 46 may be set to 500 ml/min and the flow rate of the flux-pump outlet 48 may be set to 470 ml/min. Preferably, in this step, the arterial hose clamp 22 and the venous hose clamp 20 are open and the arterial blood pump 24 is not rotating. Preferably, step (3) is stopped in a time-controlled manner. That is, when a predetermined time period has elapsed (for example 40 seconds), it is assumed that the dialyzer 6 has been suitably filled with (dialysis) liquid.

Finally, at (4) 'push/pull universal' in FIG. 3, the push-pull method forming the core aspect of the present disclosure is executed. As becomes clear with reference to FIG. 4, the push-pull method according to the disclosure is divided into two cycles, namely the push/or press cycle A and the pull/or suck cycle B, which are repeated/alternated cyclically.

In the push-pull method, a (dialysis) liquid is basically delivered from the dialysis liquid circuit 8 via the membrane 10 of the dialyzer 6 to the extracorporeal circuit 4 for priming. First, a pressure is built up in the dialyzer 6 on the dialysis liquid side/in the dialysis liquid circuit 8. This is performed according to the disclosure preferably in that the flux-pump inlet 46 and the flux-pump outlet 48 are driven by the control unit 54 in such a way that a flow rate of the flux-pump inlet 46 is (substantially) greater than a flow rate of the flux-pump outlet 48. For example, the flux-pump inlet 46 and the flux-pump outlet 48 are operated with a flow-rate difference of about 400 ml/min, such that more (dialyzing) liquid is pressed into the dialyzer 6 by the flux-pump inlet 46 than is withdrawn by the flux-pump outlet 48.

Due to this large flow (rate) difference on the dialysis liquid side, a relatively large (according to amount) negative transmembrane pressure (TMP) is generated in the dialyzer 6.

According to the disclosure, so that the transmembrane pressure (TMP) does not fall below or exceed according to amount the maximum permissible transmembrane, the compressor or the gauge/level regulation pump 32 in the extracorporeal circuit 4 is suitably driven. In principle, the compressor 32 can both push air into the extracorporeal circuit/the A/V hose system 4 and remove air from the extracorporeal circuit/the A/V hose system 4.

The compressor 32 supports the transfer of the (dialyzing) liquid through the membrane 10 of the dialyzer 6 in the suck/pull cycle B by pulling the air out of the extracorporeal circuit 4. Since the provided air trap or expansion chamber 16 (first configuration example) or the provided air traps or expansion chambers 16 and 56 (second configuration example) may collapse during the extraction or removal of air from the extracorporeal circuit, a further cycle, namely the press/or push cycle A, is integrated into the method sequence or control sequence in accordance with the present disclosure. In the press/or push cycle, air is forced into the extracorporeal circuit 4 by the compressor/gauge/level regulation pump 32. The press cycle neutralizes the negative pressure prevailing in the extracorporeal circuit 4 in stages. Cycles A and B can be changed either in a sensor-controlled or time-controlled manner.

At the beginning of the method/or control sequence, the pressure cycle A is preferably executed, which positively influences the transmembrane pressure. In other words, the transmembrane pressure increases when air from the compressor 32 is pushed into the extracorporeal circuit 4. When the transmembrane pressure exceeds a first predetermined threshold value x, which is, for example, −400 mmHg, there is a change to the suck cycle B. In the suck cycle B, air is drawn out of the extracorporeal circuit 4 via the compressor 32 until the transmembrane pressure falls below a second predetermined threshold value y, which is, for example, −420 mmHg. Then the press cycle A described above is executed again.

Figure 4:
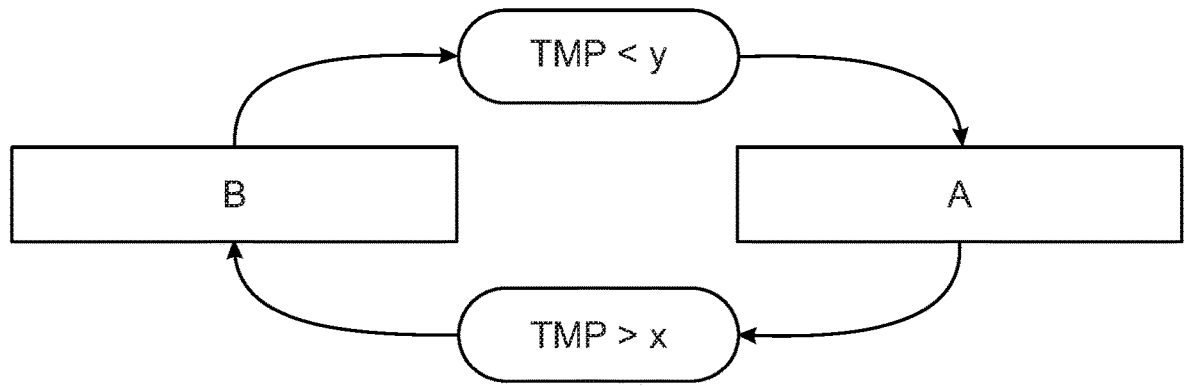
FIG. 4 shows a flow chart of the push-pull method according to the present disclosure.

The press cycle A and the suck cycle B are therefore repeated cyclically according to the diagram in FIG. 4.

Figure 5:
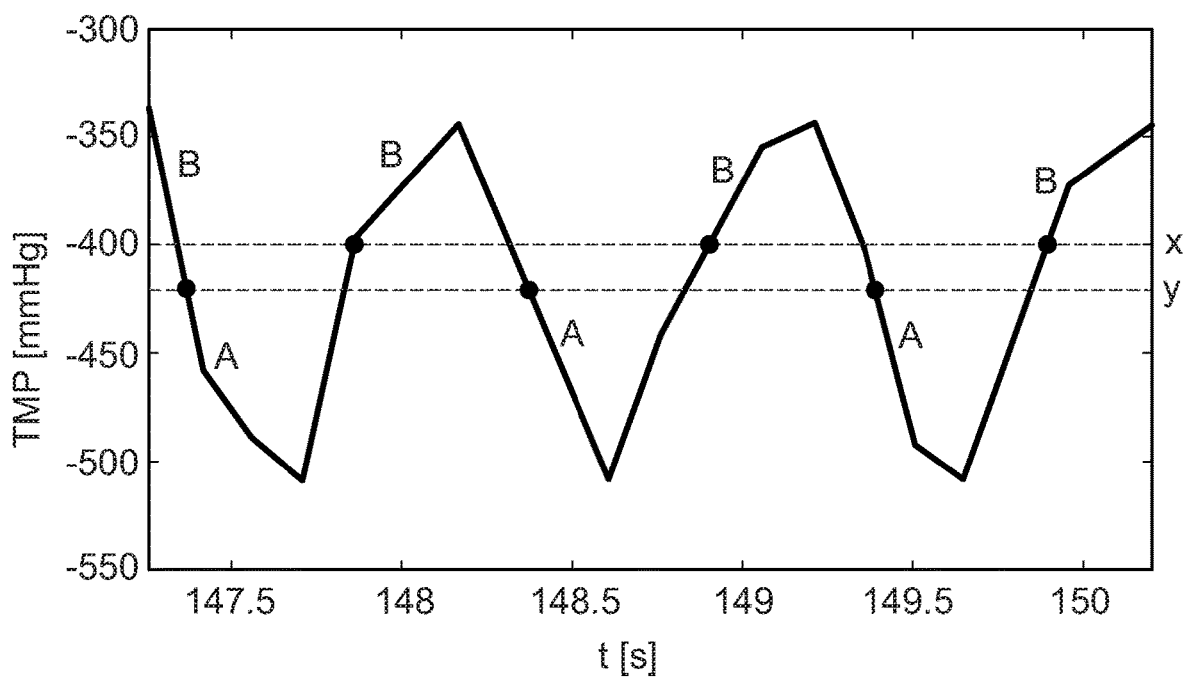
FIG. 5 shows a diagram illustrating the progression of the transmembrane pressure in the push-pull method according to the present disclosure.

FIG. 5 illustrates the course of the transmembrane pressure when the push-pull method is used according to the present disclosure. Here, it is clear that even when switching from the suck cycle B to the press cycle A at y, the transmembrane pressure initially continues to drop before it is finally positively influenced in the press cycle after reaching a lower peak point and increases accordingly. Also, when changing again from press cycle A to suck cycle B at x, it is noticeable that the transmembrane pressure initially continues to increase before it is finally negatively influenced in the suck cycle after reaching an upper peak and drops accordingly.

When the first predetermined threshold value x and the second predetermined threshold value y are suitably selected, it can be achieved that the transmembrane pressure TMP moves within a desired range and does not fall below or exceeds according to amount a maximum permissible transmembrane pressure. As can be seen from the time data in FIG. 5, the change between press cycle A and suck cycle B takes place at relatively short intervals of about 0.5 seconds.

According to the disclosure, it may be provided that during the push-pull method the venous hose clamp 20 is driven (i.e. opened or closed) in a suitable manner to support the push-pull method. For example, a negative pressure may be built up/achieved more quickly in the suck cycle when the venous hose clamp 20 is closed. Furthermore, if high-flux dialyzers are used for the priming according to the disclosure, there is a risk that the venous air trap 16 (first configuration example) or the venous air trap 16 and the arterial air trap 56 (second configuration example) fill with (dialyzing) liquid and, if applicable, the hydrophobic filters 40, 58 are moistened, so that with high-flux dialyzers it may be necessary to briefly open the venous hose clamp 20 at predetermined short time intervals (for example every 0.5 seconds).

The push-pull method according to the disclosure essentially provides a compromise solution which is applicable to both high-flux dialyzers and low-flux dialyzers. However, according to the present disclosure, it has been found to be advantageous if at least two different push-pull methods, namely the 'push/pull universal' method (see (4) in FIG. 3) and a 'push/pull low flux' method (see (5) in FIG. 3), are carried out.

For example, it is possible to change from (4) 'push/pull universal' to (5) 'push/pull low flux' if a predetermined time period for which 'push/pull universal' is performed is exceeded. This predetermined time period may be set at about 75 seconds, for example.

In particular, the 'push/pull universal' method, which is performed first according to the present disclosure, may be more adapted to the requirements of high-flux dialyzers (for example, the suck cycle may be set shorter), whereas, on the other hand, the 'push/pull low flux' method may be specifically adapted to the requirements of low-flux dialyzers (for example, the suck cycle may be set longer or the venous hose clamp 20 may be closed continuously).

If a longer time period has already elapsed in the 'push/pull universal' method and the method has not yet been stopped, this indicates that the transfer of (dialyzing) liquid via the membrane 10 of the dialyzer 6 is proving difficult and that the dialyzer 6 used is a low-flux dialyzer. In this case, according to the disclosure, a push-pull method adapted to a low-flux dialyzer is provided.

The push-pull method is finally stopped as soon as the safety air detector 18 detects liquid (dialysis liquid). As soon as this is the case, there is a transition to (6) 'priming filling slowly' (from (4) or from (5)) in FIG. 3.

In step (6), the extracorporeal circuit 4 is slowly filled with (dialysis) liquid. The flux-pump inlet 46 and the flux-pump outlet 48 are preferably operated with a flow-rate difference. For example, a flow-rate difference of 400 ml/min may be provided, wherein a flow rate of 600 ml/min is set for the flux-pump inlet 46, and a flow rate of 200 ml/min is set for the flux-pump outlet 48. The arterial blood pump 24 is preferably operated in the forward direction, for example at 150 ml/min. The arterial hose clamp 22 and the venous hose clamp 20 are preferably open.

In principle, the compressor or the gauge/or level regulation pump 32 can also be driven in a suitable manner in step (6) (for example by pulling air out of the extracorporeal circuit 4) in order to support the 'priming filling slowly' step. For example, if the safety air detector 18 does not detect (any more) (dialyzing) liquid, i.e., the liquid flow is not continuous, and at the same time the transmembrane pressure is above a threshold value (for example, −420 mmHg), the compressor 32 may pull air out of the extracorporeal circuit 4. The compressor 32 may be stopped again when the transmembrane pressure is below the threshold value, or when the venous pressure sensor 30 measures a pressure that is below a predetermined threshold value (for example, 200 mmHg).

In step (6) 'priming filling slowly', the pressure in the extracorporeal circuit 4 basically increases continuously. When the venous pressure sensor 30 detects a pressure that is above a predetermined threshold value, for example 500 mmHg, the extracorporeal circuit 4 is largely filled and the method proceeds to step (7) 'priming filling fast'.

Step (7) 'priming filling fast' is basically very similar to step (6) 'priming filling slowly'. Only the delivery or flow rates of the arterial blood pump 24, of the flux-pump inlet 46 and of the flux-pump outlet 48 are changed.

Preferably, the flow rate of the arterial blood pump 24 is increased, for example from 150 ml/min to 300 ml/min. As a result, any air bubbles still present are entrained and extracted at the venous air trap 16 (first configuration example) or the venous air trap 16 and the arterial air trap 56 (second configuration example). The flow-rate difference at the dialysis liquid side is preferably increased, for example from 400 ml/min to 600 ml/min, at a flow rate of the flux-pump inlet 46 of 700 ml/min and a flow rate of the flux-pump outlet 48 of 100 ml/min. With an increased flow rate on the side of the extracorporeal circuit 4, a poorer transfer of (dialysis) liquid via the membrane 10 of the dialyzer 6 can generally be observed. Therefore, the flow rate difference on the side of the dialysis liquid circuit 8 was increased in order to improve the transfer.

In order for the (dialysis) liquid to circulate in the extracorporeal circuit 4, the venous hose clamp 20 and the arterial hose clamp 22 have to be open. Analogous to the previous step (6) 'priming filling slowly', the compressor or the level regulation pump 32 can be appropriately driven in case of a discontinuous liquid flow in the extracorporeal circuit 4 in order to raise the liquid gauge in the air trap 16 or in the air traps 16, 56, respectively. In order to avoid uncontrolled filling of the air trap 16 or of the air traps 16, 56 when the compressor 32 is activated, the compressor 32 is switched off when the venous pressure sensor detects a pressure that is lower than a predetermined value, for example 200 mmHg. Step (7) is stopped in a time-controlled manner, in particular when a predetermined time period has elapsed, for example 25 seconds.

After the time-controlled stop of step (7) 'priming filling fast', the sequence optionally continues to step (8) 'lowering venous pressure'. Step (8) can generally be used with all low-flux dialyzers and most high-flux dialyzers. The aim of step (7) is to lower the venous pressure, which has risen sharply in the two previous steps (5) and (6). In order to lower the venous pressure, the valves upstream of the compressor or of the level regulation pump 32, i.e. the first valve 34, the second valve 36 and the third valve 38, are preferably switched in such a way that pressure equalization with the ambient air can take place. As a result, the level in the venous air trap 16 increases. In order to prevent an uncontrolled increase in the level of the venous air trap 16, step (7) is preferably stopped when the venous pressure falls below a predetermined threshold value, for example 200 mmHg.

In step (8), the flux-pump inlet 46 and the flux-pump outlet 48 are operated with a small flow rate difference. For example, the flow rate of the flux-pump inlet 46 is set to 500 ml/min, and the flow rate of the flux-pump outlet 48 is set to 470 ml/min. The arterial blood pump 24 preferably rotates clockwise, that is, in the forward direction, for example, at a flow rate of 150 ml/min. The venous hose clamp 20 and the arterial hose clamp 22 are preferably open to allow the liquid to circulate in the extracorporeal circuit 4.

After step (8), the method sequence continues to step (9) 'circulate backwards'. In this step, the arterial blood pump 24 is operated in reverse, i.e. counterclockwise, for example at a flow rate of 300 ml/min, in order to remove any remaining air bubbles from the dialyzer 6. Also in step (9), the flux-pump inlet 46 and the flux-pump outlet 48 are operated at a low flow-rate difference (for example, flux-pump inlet 46 at 500 ml/min and flux-pump outlet 48 at 470 ml/min). The venous hose clamp 20 and the arterial hose clamp 22 are preferably still open. The compressor 32 is preferably not operated. Preferably, this step is performed only for the extracorporeal blood treatment device 2 according to the first embodiment shown in FIG. 1. Step (9) is preferably stopped in a time-controlled manner (for example, after about 25 seconds).

After step (9), the method sequence continues to step (10) 'circulate forward'. In this method step, the liquid is circulated in the forward direction (clockwise) in order to separate any remaining air bubbles in the extracorporeal circuit 4, which were extracted from the dialyzer 6 during the reverse circulation, via the venous air trap 16. Basically, the flux-pump inlet 46 and the flux-pump outlet 48 are operated at slight flow-rate difference (therapy parameter), for example, the flux-pump inlet 46 at 500 ml/min and the flux-pump outlet 48 at 470 ml/min, the arterial blood pump 24 rotates in the forward direction (clockwise), approximately at 300 ml/min, and the venous hose clamp 20 and the arterial hose clamp 22 are open.

However, as in step (6) 'priming filling slowly', the compressor 32 may in principle also pull air from the extracorporeal circuit 4, in particular when the safety air detector 18 no longer registers (dialyzing) liquid and the transmembrane pressure is above a predetermined threshold value, for example −420 mmHg. In this case, a larger flow difference (e.g. 600 ml/min) between the flux-pump inlet 46 and the flux-pump outlet 48 can be set. For example, the flow rate of flux-pump inlet 46 could be set to 700 ml/min and the flow rate of the flux-pump outlet 48 could be set to 100 ml/min. Due to the larger flow difference, it can be achieved that more (dialyzing) liquid passes through the membrane 10 of the dialyzer 6 and thus a continuous liquid flow is established in the extracorporeal circuit 4, in particular in the venous portion 14 behind the venous air trap 16.

Preferably, the compressor 32 is stopped here (stop criterion) when the venous pressure sensor 30 measures a venous pressure that is less than 0 mmHg. The stop criterion for pulling the compressor 32 has thus changed compared to the previous steps. The reason for this is that the venous pressure has already decreased (monotonically) during steps (9) and (10) while air was continuously extracted from the extracorporeal circuit 4. For this reason, it is necessary that a safety threshold of the level regulation also decreases.

As previously described, the compressor or level regulation pump 32 draws air from the extracorporeal circuit 4 as soon as the safety air detector 18 detects air. As a result, the level of the venous air trap 16 increases. Due to the previous backward circulation, many air bubbles are present in the extracorporeal circuit 4. If a number of air bubbles exist at the safety air detector 18, this would lead to an uncontrolled rise in the level in the venous air trap 16, since the pulling by the compressor 32 would be carried out several times in succession. In order to counteract this unwanted sequence, it is necessary to block the pulling for a predetermined period of time (for example, the first 5 seconds). After that, a normal program sequence can be resumed.

Step (10) 'circulate forward' is basically terminated when a predetermined time, for example 25 seconds, has elapsed.

After step (10), at step (11) 'set air trap', the level of the venous air trap 16 (for the first configuration example) or, respectively, the levels of the venous air trap 16 and of the arterial air trap 56 (for the second configuration example) are set.

When the overall preparation of the extracorporeal blood treatment device 2 is complete, therapy can take place at step (12). The connection between the arterial portion 12 and the venous portion 14 (on the adapter/connector 15) is disconnected and the arterial portion 12 is connected to a patient. The arterial blood pump 24 rotates and draws blood from the patient. (Dialysis) liquid present in the extracorporeal circuit 4 is drained. As soon as the extracorporeal circuit 4 is sufficiently filled with blood, the venous portion 14 is also connected to the patient and the therapy can begin.

The total run time of the process shown in FIG. 3 is about 4 to 5 min for high-flux dialyzers, and about 10 to 15 min for low-flux dialyzers.

The invention claimed is:

1. An extracorporeal blood treatment device prepared for an automatic priming thereof, comprising:
    an extracorporeal circuit;
    a flow machine connected to the extracorporeal circuit;
    a dialysis liquid circuit;
    a dialyzer comprising:
        a dialysis liquid circuit side defining a portion of the dialysis liquid circuit,
        an extracorporeal circuit side defining a portion of the extracorporeal circuit, and
        a membrane separating the dialysis liquid circuit side from the extracorporeal circuit side;
    a control unit; and
    at least one of:
        one or more control valves in the dialysis liquid circuit, or
        one or more pumps in the dialysis liquid circuit;
    wherein the control unit is configured to prime the extracorporeal circuit and the extracorporeal circuit side of the dialyzer by:
        controlling the one or more control valves and/or the one or more pumps to generate a build-up of a pressure in a liquid in the dialysis liquid circuit side of the dialyzer, and
        controlling the flow machine to alternately perform a push/or press cycle, in which the flow machine pushes air into the extracorporeal circuit from outside the extracorporeal circuit, and a pull/or suck cycle, in which the flow machine pulls air out of the extracorporeal circuit, to thereby support a transfer of the liquid via the membrane from the dialysis liquid circuit side of the dialyzer to the extracorporeal circuit side of the dialyzer.

2. The extracorporeal blood treatment device according to claim 1, wherein the one or more control valves and/or the one or more pumps comprise a flux-pump inlet in the dialysis liquid circuit upstream of the dialyzer and a flux-pump outlet in the dialysis liquid circuit downstream of the dialyzer, and the control unit is configured to control the flux-pump inlet and the flux-pump outlet to build up the pressure in the dialyzer on the dialysis liquid circuit side of the dialyzer in such a way that a respective flow rate of the flux-pump inlet is greater than a respective flow rate of the flux-pump outlet.

3. The extracorporeal blood treatment device according to claim 1, wherein the extracorporeal circuit comprises an expansion chamber, and the flow machine is a compressor or a gauge/level regulation pump that is arranged downstream of the expansion chamber or is connected to the expansion chamber, wherein the control unit is configured to operate the compressor or the gauge/level regulation pump to press the air into the expansion chamber or such the air out of the expansion chamber.

4. The extracorporeal blood treatment device according to claim 1, wherein the control unit is configured to cyclically alternate and repeat the push/or press cycle and the pull/or suck cycle.

5. The extracorporeal blood treatment device according to claim 4, wherein the control unit is configured to stop the cyclic alternation of the push/or press cycle and the pull/or suck cycle when a safety air detector provided in a venous portion of the extracorporeal circuit detects the liquid.

6. The extracorporeal blood treatment device according to claim 1, wherein the dialyzer is a low-flux dialyzer with an ultrafiltration coefficient of less than 15 ml/(h*mmHg).

7. The extracorporeal blood treatment device according to claim 1, wherein the control unit is configured to switch between the push/or press cycle and the pull/or suck cycle in a sensor-controlled and/or time-controlled manner.

8. The extracorporeal blood treatment device according to claim 1, wherein the control unit is configured to first perform the push/or press cycle and to perform the pull/or suck cycle after performing the push/or press cycle for a first time.

9. The extracorporeal blood treatment device according to claim 1, wherein the control unit is configured to switch from the push/or press cycle to the pull/or suck cycle when a transmembrane pressure between the dialysis liquid circuit side and the extracorporeal circuit side exceeds a first predetermined threshold value, and to switch from the pull/or suck cycle to the push/or press cycle when the transmembrane pressure between the dialysis liquid circuit side and the extracorporeal circuit side falls below a second predetermined threshold value.

10. The extracorporeal blood treatment device according to claim 9, wherein the first predetermined threshold value is greater than the second predetermined threshold value.

11. A method for automatically priming an extracorporeal blood treatment device comprising an extracorporeal circuit, a flow machine in the extracorporeal circuit, a dialysis liquid circuit, a control unit, one or more control valves and/or one or more pumps in the dialysis liquid circuit, and a dialyzer comprising a dialysis liquid circuit side of the dialyzer defining a portion of the dialysis liquid circuit, an extracorporeal circuit side of the dialyzer defining a portion of the extracorporeal circuit, and a membrane in the dialyzer and separating the dialysis liquid circuit side from the extracorporeal circuit side, the method comprising
controlling the control unit to operate the one or more control valves and/or the one or more pumps to prime the extracorporeal circuit and the extracorporeal circuit side of the dialyzer by:
controlling the control unit to operate the one or more control valves and/or the one or more pumps to build up pressure in a liquid in the dialysis liquid circuit side of the dialyzer; and
controlling the control unit to operate the flow machine to cyclically alternate between a push/or press cycle to push air into the extracorporeal circuit from outside the extracorporeal circuit, and a pull/or suck cycle to pull air out of the extracorporeal circuit, and thereby support transfer of the liquid via the membrane from the dialysis liquid circuit side of the dialyzer to the extracorporeal circuit side of the dialyzer.

12. The extracorporeal blood treatment device according to claim 1, wherein:
the extracorporeal circuit comprises at least one expansion chamber,
the flow machine is connected to the at least one expansion chamber, and
the flow machine is configured to pump air into the at least one expansion chamber during the push/or press cycle and pull air out of the at least one expansion chamber during the pull/or suck cycle.

13. The extracorporeal blood treatment device according to claim 12, wherein the flow machine is connected to the at least one expansion chamber by a line, wherein the line contains a hydrophobic filter.

* * * * *